(12) United States Patent
Sembo et al.

(10) Patent No.: US 6,201,017 B1
(45) Date of Patent: Mar. 13, 2001

(54) ECTOPARASITE CONTROLLING AGENT FOR ANIMALS

(75) Inventors: Satoshi Sembo, Takarazuka; Mitsuyasu Makita, Nishinomiya, both of (JP)

(73) Assignee: Sumitomo Chemical Co., Ltd., Osaka (JP)

( * ) Notice: Subject to any disclaimer, the term of this patent is extended or adjusted under 35 U.S.C. 154(b) by 0 days.

(21) Appl. No.: 09/400,299

(22) Filed: Sep. 21, 1999

Related U.S. Application Data

(63) Continuation-in-part of application No. 09/299,885, filed on Apr. 27, 1999, now abandoned.

(30) Foreign Application Priority Data

| Jul. 27, 1998 | (JP) | 10-210875 |
| Oct. 28, 1998 | (JP) | 10-306960 |
| Jun. 10, 1999 | (JP) | 11-163727 |

(51) Int. Cl.[7] .......... A01N 47/06; A01N 43/00; A01N 25/00; A01N 31/00; A01N 33/00; A01N 37/52

(52) U.S. Cl. .......... 514/471; 424/405; 514/408; 514/424; 514/461; 514/463; 514/467; 514/512; 514/579; 514/634; 514/715; 514/723; 514/724; 514/730; 514/772; 514/785; 514/875; 514/975

(58) Field of Search .................. 514/975, 461, 514/634, 740, 875, 579, 408, 424, 463, 467, 471, 512, 715, 723, 724, 730, 772, 785, 788; 424/405

(56) References Cited

U.S. PATENT DOCUMENTS

| 4,742,060 | 5/1988 | Shiokawa et al. | 514/252 |
| 4,849,432 | 7/1989 | Shiokawa et al. | 514/341 |
| 5,034,404 | 7/1991 | Uneme et al. | 514/365 |
| 5,304,566 | 4/1994 | Ishimitsu et al. | 514/357 |
| 5,532,365 | 7/1996 | Kodaka et al. | 544/212 |

FOREIGN PATENT DOCUMENTS

| 2014495 | 11/1995 | (AU) . |
| 0061208A1 | 9/1982 | (EP) . |
| 0428941A1 | 5/1991 | (EP) . |
| 0682869A1 | 11/1995 | (EP) . |
| 9740692A1 | 6/1997 | (WO) . |
| 9737544A1 | 10/1997 | (WO) . |
| 9817277A1 | 4/1998 | (WO) . |
| 9842191A1 | 10/1998 | (WO) . |
| 9941987A1 | 8/1999 | (WO) . |

OTHER PUBLICATIONS

Robert G. Arther, Ph. D. et al; Efficacy of imidacloprid for removal and control of fleas (Ctenocephalides felis) on dogs; AJVR, vol. 58, No. 8, pp. 848–850, Aug. 1997.

*Primary Examiner*—John Pak
*Assistant Examiner*—Frank Choi
(74) *Attorney, Agent, or Firm*—Birch, Stewart, Kolasch & Birch, LLP

(57) ABSTRACT

An ectoparasite-controlling agent for animals comprising 0.1 to 20% by weight of the neonocotinoid compounds defined in the specification and 10 to 95% by weight of a glycol or glycol monoalkyl ether has an excellent effectiveness by the application methods such as spot-on and pour-on application.

5 Claims, No Drawings

ECTOPARASITE CONTROLLING AGENT FOR ANIMALS

CROSS REFERENCES TO RELATED APPLICATIONS

This is a continuation-in-part application of Ser. No. 09/299,885 filed on Apr. 27, 1999, now abandoned.

FIELD OF THE INVENTION

The present invention relates to ectoparasite controlling agents, and more specifically relates to an excellent ectoparasite controlling agent for animals which is used for regional application methods such as spot-on or pour-on application and a method for controlling ectoparasites of animals.

BACKGROUND OF THE INVENTION

Heretofore, as an application method to control harmful pests that injure domestic animals such as pets and farm animals, particularly ectoparasites such as fleas (Pulicidae), lice (Anoplura) and ticks (Acarina), methods of application recognized as spot-on and pour-on applications have been known, and because these methods of applications have been elementary, they are utilized in the concerning ectoparasite controlling.

However, it was not common to have the active ingredients contained in the ectoparasite controlling agents to be always sufficiently effective.

SUMMARY OF THE INVENTION

The present invention provides an ectoparasite controlling agent for animals having an ability to exert an excellent efficacy against ectoparasites from spot-on or pour-on applications, with the incorporation of a neonicotinoid compound and a glycol or a specific glycol derivative, as well as from the specialized mixing ratio of that incorporation.

More specifically, the present invention is an ectoparasite controlling agent for animals (hereinafter, the present agent (s)) which is a liquid formulation comprising 10 to 95% by weight of a glycol or glycol monoalkyl ether (e.g. $C_{1-4}$ alkyl ether) and 0.1 to 20% by weight of the neonicotinoid compound given in the following formula (1), (2) or (3) (herein after, the present compound(s)):

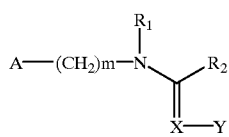

(1)

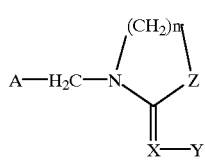

(2)

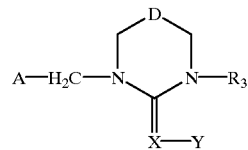

(3)

(wherein, A represents a 6-chloro-3-pyridyl, 2-chloro-5-thiazolyl, tetrahydrofuran-2-yl, tetrahydrofuran-3-yl, 5-methyltetrahydrofuran-3-yl, 3-pyridyl, 6-bromo-3-pyridyl, 3-cyanophenyl, 2-methyl-5-thiazolyl, 2-phenyl-5-thiazolyl or 2-bromo-5-thiazolyl group;

$R_1$ represents a hydrogen atom, methyl, ethyl, formyl or acetyl group;

$R_2$ represents a methyl, amino, methylamino, N,N-dimethylamino, ethylamino, N,N-diethylamino, N-methyl-N-ethylamino, 1-pyrrolidinyl, (6-chloro-3-pyridyl)methylamino or N-methyl-N-(6-chloro-3-pyridyl)methylamino group;

$R_3$ represents a methyl, ethyl, propyl, propenyl or propynyl group;

X represents a nitrogen atom or CH group;

Y represents a cyano, nitro or trifluoroacetyl group;

Z represents a NH group or sulfur atom;

D represents an oxygen atom or —N(CH$_3$)—group;

m represents an integer of 0 or 1; and n represents an integer of 2 or 3)

as well as, a method for controlling ectoparasites of animals.

DETAILED DESCRIPTION OF THE INVENTION

The present compounds are known as an active ingredient for pesticides, and described in, for example, U.S. Pat. Nos. 5,532,365, 4,742,060, 4,849,432, 5,034,404, 5,750,548, 5,304,566 and EP-428941A. The present compound is comprised from 0.1 to 20% by weight, preferably from 1 to 15% by weight, and more preferably from 5 to 10% by weight in the present agent.

As the compound given in the formula (1), for example, (E)-N$^1$-[(6-chloro-3-pyridyl)methyl]-N$^2$-cyano-N$^1$-methylacetamidine, N-[(6-chloro-3-pyridyl)methyl]-N-ethyl-N'-methyl-2-nitro-1,1-ethylidenediamine, 1-(6-chloro-3-pyridyl)methyl-3-methyl-2-cyanoguanidine, 1-(6-chloro-3-pyridyl)methyl-1,3-dimethyl-2-cyanoguanidine, 1-(6-chloro-3-pyridyl)methyl-1-ethyl-3-methyl-2-cyanoguanidine, 1-(6-chloro-3-pyridyl)methyl-1,3-dimethyl-3-(6-chloro-3-pyridyl)methyl-2-cyanoguanidine, 1-(6-chloro-3-pyridyl)methyl-3-methyl-2-nitroguanidine, 1-(6-chloro-3-pyridyl)methyl-3,3-dimethyl-2-nitroguanidine, 1-(6-chloro-3-pyridyl)methyl-1-methyl-2-nitroguanidine, 1-(6-chloro-3-pyridyl)methyl-1,3-dimethyl-2-nitroguanidine, 1-(6-chloro-3-pyridyl)methyl-3-ethyl-2-nitroguanidine, 1-(6-chloro-3-pyridyl)methyl-3-(6-chloro-3-pyridyl)methyl-2-nitroguanidine, 1-(6-chloro-3-pyridyl)methyl-3-methyl-2-trifluoroacetylguanidine, 1-(6-chloro-3-pyridyl)methyl-1-ethyl-3-methyl-2-nitroguanidine, 1-(6-chloro-3-pyridyl)methyl-1,3,3-trimethyl-2-nitroguanidine, 1-(6-chloro-3-pyridyl)methyl-2-nitroguanidine, 1-(6-chloro-3-pyridyl)methyl-1-ethyl-2-nitroguanidine, 1-(3-pyridyl)methyl-3-methyl-2-nitroguanidine, 1-(6-bromo-3-pyridyl)methyl-3-methyl-2-nitroguanidine, 1-(2-chloro-5- thiazolyl)methyl-3-methyl-2-nitroguanidine, 1-(3-cyanophenyl)-3-methyl-2-nitroguanidine, 1-(4-chlorophenyl)methyl-3-methyl-2-nitroguanidine, 1-(6-chloro-3-pyridyl)methyl-3,3-dimethyl-1-formyl-2-nitroguanidine, 1-(6-chloro-3-pyridyl)methyl-3,3-dimethyl-1-acetyl-2-nitroguanidine, 1-(6-chloro-3-pyridyl)-3-methyl-2-cyanoguanidine, 1-(2-chloro-5-thiazolyl)methyl-3,3-dimethyl-2-nitroguanidine, 1-(2-chloro-5-thiazolyl)methyl-1-ethyl-3-methyl-2-nitroguanidine, 1-(2-chloro-5-thiazolyl)methyl-1-acetyl-3,3-dimethyl-2-nitroguanidine, 1-(6-chloro-3-pyridyl)methyl-1-methyl-2-trifluoroacetylguanidine, 1-(2-chloro-5-thiazolyl)methyl-1,3-dimethyl-2-nitroguanidine, 1-(2-chloro-5-thiazolyl)methyl-1-methyl-2-nitroguanidine, 1-(5-thiazolyl)methyl-3-methyl-2-nitroguanidine, 1-(2-methyl-5-thiazolyl)methyl-3,3-dimethyl-2-nitroguanidine, 1-(2-methyl-5-thiazolyl)methyl-3-methyl-2-nitroguanidine, 1-(2-phenyl-5-thiazolyl)methyl-3-methyl-2-nitroguanidine, 1-(2-chloro-5-thiazolyl)methyl-3,3-diethyl-2-nitroguanidine, 1-(2-chloro-5-thiazolyl)methyl-3-methyl-3-ethyl-2-nitroguanidine, 1-(2-chloro-5-thiazolyl)methyl-3-(1-pyrrolidinyl)-2-nitroguanidine, 1-(2-chloro-5-thiazolyl)methyl-1,3,3-trimethyl-2-nitroguanidine, 1-(2-bromo-5-thiazolyl)methyl-3-methyl-2-nitroguanidine, 1-(2-bromo-5-thiazolyl)methyl-3,3-dimethyl-2-nitroguanidine, 1-(2-chloro-5-thiazolyl)methyl-3-methyl-2-cyanoguanidine, 1-(tetrahydrofuran-3-yl)methyl-3-methyl-2-nitroguanidine or 1-(tetrahydrofuran-2-yl)methyl-3-methyl-2-nitroguanidine is suitable.

As the compound given in the formula (2), for example, 3-[(6-chloro-3-pyridyl)methyl]-N-cyano-2-thiazolidineimine or 1-[(6-chloro-3-pyridyl)methyl]-N-nitrotetrahydropyrimidine-2-imine is suitable.

As the compound given in the formula (3), for example, 3-[(2-chloro-5-thiazolyl)methyl]-5-methyl-4-nitroiminotetrahydro-1,3,5-oxadiazine, 3,5-dimethyl-1-[(6-chloro-3-pyridyl)methyl]-N-nitrohexahydro-1,3,5-triazine-2-imine, 3,5-dimethyl-1-[(2-chloro-5-thiazolyl)methyl]-2-nitroiminohexahydro-1,3,5-triazine, 3-ethyl-5-methyl-1-[(6-chloro-3-pyridyl)methyl]-N-nitrohexahydro-1,3,5-triazine-2-imine, 3-n-propyl-5-methyl-1-[(6-chloro-3-pyridyl)methyl]-N-nitrohexahydro-1,3,5-triazine-2-imine, 3-n-propyl-5-methyl-1-[(2-chloro-5-thiazolyl)methyl]-N-nitrohexahydro-1,3,5-triazine-2-imine, 3-(2-propenyl)-5-methyl-1-[(6-chloro-3-pyridyl)methyl]-N-nitrohexahydro-1,3,5-triazine-2-imine or 3-(2-propynyl)-5-methyl-1-[(6-chloro-3-pyridyl)methyl]-N-nitrohexahydro-1,3,5-triazine-2-imine is suitable.

As the glycol or glycol monoalkyl ether, for example, ethylene glycol, diethylene glycol, triethylene glycol, propylene glycol, dipropylene glycol, tripropylene glycol, hexamethylene glycol, 1,3-butanediol, 3-methyl-1,3-butanediol, 2-methyl-1,3-propanediol, ethylene glycol monomethyl ether, ethylene glycol monoethyl ether, ethylene glycol monobutyl ether, diethylene glycol monomethyl ether, diethylene glycol monoethyl ether, propylene glycol monomethyl ether, propylene glycol monoethyl ether, propylene glycol monotertiarybutyl ether, dipropylene glycol monomethyl ether or 3-methoxy-3-methyl-1-butanol is suitable. The present agent comprises the glycol or glycol monoalkyl ether from 10 to 95% by weight, preferably from 30 to 90% by weight. In case that the present agent does not contain the other solvent, the preferable content of the glycol or glycol monoalkyl ether is generally from 50 to 80% by weight.

More specifically, for the present compound and the glycol in the present agent, the following are examples of suitable combinations:

(E)-$N^1$-[(6-chloro-3-pyridyl)methyl]-$N^2$-cyano-$N^1$-methylacetamidine and ethylene glycol, N-[(6-chloro-3-pyridyl)methyl]-N-ethyl-N'-methyl-2-nitro-1,1-ethylidenediamine and ethylene glycol, 1-(tetrahydrofuran-3-yl)methyl-3-methyl-2-nitroguanidine and ethylene glycol, 3-[(6-chloro-3-pyridyl)methyl]-N-cyano-2-thiazolidineimine and ethylene glycol, 3-[(2-chloro-5-thiazolyl)methyl]-5-methyl-4-nitroiminotetrahydro-1,3,5-oxadiazine and ethylene glycol, (E)-$N^1$-[(6-chloro-3-pyridyl)methyl]-$N^2$-cyano-$N^1$-methylacetamidine and diethylene glycol, N-[(6-chloro-3-pyridyl)methyl]-N-ethyl-N'-methyl-2-nitro-1,1-ethylidenediamine and diethylene glycol, 1-(tetrahydrofuran-3-yl)methyl-3-methyl-2-nitroguanidine and diethylene glycol, 3-[(6-chloro-3-pyridyl)methyl-N-cyano-2-thiazolidineimine and diethylene glycol, 3-[(2-chloro-5-thiazolyl)methyl]-5-methyl-4-nitroimninotetrahydro-1,3,5-oxadiazine and diethylene glycol, (E)-$N^1$-[(6-chloro-3-pyridyl)methyl]-$N^2$-cyano-$N^1$-methylacetamidine and triethylene glycol, N-[(6-chloro-3-pyridyl)methyl]-N-ethyl-N'-methyl-2-nitro-1,1-ethylidenediamine and triethylene glycol, 1-(tetrahydrofuran-3-yl)methyl-3-methyl-2-nitroguanidine and triethylene glycol, 3-[(6-chloro-3-pyridyl)methyl-N-cyano-2-thiazolidineimine and triethylene glycol, 3-[(2-chloro-5-thiazolyl)methyl]-5-methyl-4-nitroiminotetrahydro-1,3,5-oxadiazine and triethylene glycol, (E)-$N^1$-[(6-chloro-3-pyridyl)methyl]-$N^2$-cyano-$N^1$-methylacetamidine and propylene glycol, N-[(6-chloro-3-pyridyl)methyl]-N-ethyl-N'-methyl-2-nitro-1,1-ethylidenediamine and propylene glycol, 1-(tetrahydrofuran-3-yl)methyl-3-methyl-2-nitroguanidine and propylene glycol, 3-[(6-chloro-3-pyridyl)methyl-N-cyano-2-thiazolidineimine and propylene glycol, 3-[(2-chloro-5-thiazolyl)methyl]-5-methyl-4-nitroiminotetrahydro-1,3,5-oxadiazine and propylene glycol, (E)-$N^1$-[(6-chloro-3-pyridyl)methyl]-$N^2$-cyano-$N^1$-methylacetamidine and dipropylene glycol, N-[(6-chloro-3-pyridyl)methyl]-N-ethyl-N'-methyl-2-nitro-1,1-ethylidenediamine and dipropylene glycol, 1-(tetrahydrofuran-3-yl)methyl-3-methyl-2-nitroguanidine and dipropylene glycol, 3-[(6-chloro-3-pyridyl)methyl-N-cyano-2-thiazolidineimine and dipropylene glycol, 3-[(2-chloro-5-thiazolyl)methyl]-5-methyl-4-nitroiminotetrahydro- 1,3,5-oxadiazine and dipropylene glycol, (E)-$N^1$-[(6-chloro-3-pyridyl)methyl]-$N^2$-cyano-$N^1$-methylacetamidine and tripropylene glycol, N-[(6-chloro-3-pyridyl)methyl]-N-ethyl-N'-methyl-2-nitro-1,1-ethylidenediamine and tripropylene glycol, 1-(tetrahydrofuran-3-yl)methyl-3-methyl-2-nitroguanidine and tripropylene glycol, 3-[(6-chloro-3-pyridyl)methyl-N-cyano-2-thiazolidineimine and tripropylene glycol, 3-[(2-chloro-5-thiazolyl)methyl]-5-methyl-4-nitroiminotetrahydro-1,3,5-oxadiazine and tripropylene glycol, (E)-$N^1$-[(6-chloro-3-pyridyl)methyl]-$N^2$-cyano-$N^1$-methylacetamidine and hexamethylene glycol, N-[(6-chloro-3-pyridyl)methyl]-N-ethyl-N'-methyl-2-nitro-1,1-ethylidenediamine and hexamethylene glycol, 1-(tetrahydrofuran-3-yl)methyl-3-methyl-2-nitroguanidine and hexamethylene glycol, 3-[(6-chloro-3-pyridyl)methyl-N-cyano-2-thiazolidineimine and hexamethylene glycol, 3-[(2-chloro-5-thiazolyl)methyl]-5-methyl-4-nitroiminotetrahydro-1,3,5-oxadiazine and hexamethylene glycol, (E)-$N^1$-[(6-chloro-3-pyridyl)methyl]-$N^2$-cyano-$N^1$-methylacetamidine and 1,3-butanediol, N-[(6-chloro-3-pyridyl)methyl]-N-ethyl-N'-methyl-2-nitro-1,1 -ethylidenediamine and 1,3- butanediol, 1-(tetrahydrofuran-3-yl)methyl-3-methyl-2-nitroguanidine and 1,3-butanediol, 3-[(6-chloro-3-pyridyl)methyl-N-cyano-2-thiazolidineimine and 1,3-butanediol, 3-[(2-chloro-5-thiazolyl)methyl]-5-methyl-4-nitroiminotetrahydro-1,3,5-oxadiazine and 1,3-butanediol, (E)-N$^1$-[(6-chloro-3-pyridyl)methyl]-N$^2$-cyano-N$^1$-methylacetamidine and 3-methyl-1,3-butanediol, N-[(6-chloro-3-pyridyl)methyl]-N-ethyl-N'-methyl-2-nitro-1,1-ethylidenediamine and 3-methyl-1,3-butanediol, 1-(tetrahydrofuran-3-yl)methyl-3-methyl-2-nitroguanidine and 3-methyl-1,3-butanediol, 3-[(6-chloro-3-pyridyl)methyl-N-cyano-2-thiazolidineimine and 3-methyl-1,3-butanediol, 3-[(2-chloro-5-thiazolyl)methyl]-5-methyl-4-nitroiminotetrahydro-1,3,5-oxadiazine and 3-methyl-1,3-butanediol, (E)-N$^1$-[(6-chloro-3-pyridyl)methyl]-N$^2$-cyano-N$^1$-methylacetamidine and 2-methyl-1,3-propanediol, N-[(6-chloro-3-pyridyl)methyl]-N-ethyl-N'-methyl-2-nitro-1,1-ethylidenediamine and 2-methyl-1,3-propanediol, 1-(tetrahydrofuran-3-yl)methyl-3-methyl-2-nitroguanidine and 2-methyl-1,3-propanediol, 3-[(6-chloro-3-pyridyl)methyl-N-cyano-2-thiazolidineimine and 2-methyl-1,3-propanediol, 3-[(2-chloro-5-thiazolyl)methyl]-5-methyl-4-nitroiminotetrahydro-1,3,5-oxadiazine and 2-methyl-1,3-propanediol, (E)-N$^1$-[(6-chloro-3-pyridyl)methyl]-N$^2$-cyano-N$^1$-methylacetamidine and ethylene glycol monomethyl ether, N-[(6-chloro-3-pyridyl)methyl]-N-ethyl-N'-methyl-2-nitro-1,1-ethylidenediamine and ethylene glycol monomethyl ether, 1-(tetrahydrofuran-3-yl)methyl-3-methyl-2-nitroguanidine and ethylene glycol monomethyl ether, 3-[(6-chloro-3-pyridyl)methyl-N-cyano-2-thiazolidineimine and ethylene glycol monomethyl ether, 3-[(2-chloro-5-thiazolyl)methyl]-5-methyl-4-nitroiminotetrahydro-1,3,5-oxadiazine and ethylene glycol monomethyl ether, (E)-N$^1$-[(6-chloro-3-pyridyl)methyl]-N$^2$-cyano-N$^1$-methylacetamidine and ethylene glycol monoethyl ether, N-[(6-chloro-3-pyridyl)methyl]-N-ethyl-N'-methyl-2-nitro-1,1-ethylidenediamine and ethylene glycol monoethyl ether, 1-(tetrahydrofuran-3-yl)methyl-3-methyl-2-nitroguanidine and ethylene glycol monoethyl ether, 3-[(6-chloro-3-pyridyl)methyl-N-cyano-2-thiazolidineimine and ethylene glycol monoethyl ether, 3-[(2-chloro-5-thiazolyl)methyl]-5-methyl-4-nitroiminotetrahydro-1,3,5-oxadiazine and ethylene glycol monoethyl ether, (E)-N$^1$-[(6-chloro-3-pyridyl)methyl]-N$^2$-cyano-N$^1$-methylacetamidine and ethylene glycol monobutyl ether, N-[(6-chloro-3-pyridyl)methyl]-N-ethyl-N'-methyl-2-nitro-1,1-ethylidenediamine and ethylene glycol monobutyl ether, 1-(tetrahydrofuran-3-yl)methyl-3-methyl-2-nitroguanidine and ethylene glycol monobutyl ether, 3-[(6-chloro-3-pyridyl)methyl-N-cyano-2-thiazolidineimine and ethylene glycol monobutyl ether, 3-[(2-chloro-5-thiazolyl)methyl]-5-methyl-4-nitroiminotetrahydro- 1,3,5-oxadiazine and ethylene glycol monobutyl ether, (E)-N$^1$-[(6-chloro-3-pyridyl)methyl]-N$^2$-cyano-N$^1$-methylacetamidine and propylene glycol monomethyl ether, N-[(6-chloro-3-pyridyl)methyl]-N-ethyl-N'-methyl-2-nitro-1,1-ethylidenediamine and propylene glycol monomethyl ether, 1-(tetrahydrofuran-3-yl)methyl-3-methyl-2-nitroguanidine and propylene glycol monomethyl ether, 3-[(6-chloro-3-pyridyl)methyl-N-cyano-2-thiazolidineimine and propylene glycol monomethyl ether, 3-[(2-chloro-5-thiazolyl)methyl]-5-methyl-4-nitroiminotetrahydro-1,3,5-oxadiazine and propylene glycol monomethyl ether, (E)-N$^1$-[(6-chloro-3-pyridyl)methyl]-N$^2$-cyano-N$^1$-methylacetamidine and propylene glycol monoethyl ether, N-[(6-chloro-3-pyridyl)methyl]-N-ethyl-N'-methyl-2-nitro-1,1-ethylidenediamine and propylene glycol monoethyl ether, 1-(tetrahydrofuran-3-yl)methyl-3-methyl-2-nitroguanidine and propylene glycol monoethyl ether, 3-[(6-chloro-3-pyridyl)methyl-N-cyano-2-thiazolidineimine and propylene glycol monoethyl ether, 3-[(2-chloro-5-thiazolyl)methyl]-5-methyl-4-nitroiminotetrahydro-1,3,5-oxadiazine and propylene glycol monoethyl ether, (E)-N$^1$-[(6-chloro-3-pyridyl)methyl]-N$^2$-cyano-N$^1$-methylacetamidine and propylene glycol monotertiarybutyl ether, N-[(6-chloro-3-pyridyl)methyl]-N-ethyl-N'-methyl-2-nitro-1,1-ethylidenediamine and propylene glycol monotertiarybutyl ether, 1-(tetrahydrofuran-3-yl)methyl-3-methyl-2-nitroguanidine and propylene glycol monotertiarybutyl ether, 3-[(6-chloro-3-pyridyl)methyl-N-cyano-2-thiazolidineimine and propylene glycol monotertiarybutyl ether, 3-[(2-chloro-5-thiazolyl)methyl]-5-methyl-4-nitroiminotetrahydro-1,3,5-oxadiazine and propylene glycol monotertiarybutyl ether, (E)-N$^1$-[(6-chloro-3-pyridyl)methyl]-N$^2$-cyano-N$^1$-methylacetamidine and 3-methoxy-3-methyl-1-butanol, N-[(6-chloro-3-pyridyl)methyl]-N-ethyl-N'-methyl-2-nitro-1,1-ethylidenediamine and 3-methoxy-3-methyl-1-butanol, 1-(tetrahydrofuran-3-yl) methyl-3-methyl-2-nitroguanidine and 3-methoxy- 3-methyl-1-butanol, 3-[(6-chloro-3-pyridyl)methyl-N-cyano-2-thiazolidineimine and 3-methoxy-3-methyl-1-butanol, 3-[(2-chloro-5-thiazolyl)methyl]-5-methyl-4-nitroiminotetrahydro-1,3,5-oxadiazine and 3-methoxy-3-methyl-1-butanol and so on.

The present agent is a liquid formulation comprising 10 to 95% by weight of a glycol or glycol monoalkyl ether and 0.1 to 20% by weight of the present compound, and may comprise, optionally, for example, liquid carriers such as $C_{1-4}$ alcohols (e.g. methanol, ethanol, isopropyl alcohol, tert-butyl alcohol), benzyl alcohol, propylene carbonate, N-methyl-2-pyrrolidone and water. Said liquid carrier is preferably the solvent that is miscible with a glycol or glycol monoalkyl ether and the amount of the solvent is usually 3 to 85% by weight or less, preferably 3 to 70% by weight or less in case that the solvent is utilized. The present agent may further comprise auxiliaries. Examples of the auxiliaries include anti-oxidents such as BHT and BHA; emulsifiers such as sorbitan monooleate, sorbitan monolaurate, caprylic acid monoglyceride, capric acid monoglyceride, isostearic acid monoglyceride and propylene glycol monocaprylate; and oxyacid esters such as triethyl citrate. Particularly, an addition of benzyl alcohol is preferable in view of improving solubility.

The present agent may also comprise, optionally, active ingredients other than the present compound.

The active ingredients are, for example, pyrethroid compounds such as permethrin, phenothrin, allethrin, pyrethrin, cyphenothrin, cyfluthrin, fenvalerate, fenpropathrin and transfluthrin; organophosphorus compounds such as dichlorvos, tetrachlorvinphos, fenthion, chlorpyrifos and diazinon; carbamate compounds such as propoxur, carbaryl, metoxadiazone and fenobucarb; chitin-synthesis inhibiting substances such as lufenuron, chlorfluazuron, hexaflumuron, cyromazine and 1-(2,6-difluorobenzoyl)- 3-[2-fluoro-4-(1,1,2,3,3,3-hexafluoropropoxy)phenyl]urea; juvenile hormone analogues such as pyriproxyfen, methoprene, hydroprene and fenoxycarb; N-phenylpyrazole compounds; endoparasite controlling substances for animals such as milbemycin, abamectin and avermectin; pest repelling compounds such as N,N-diethyl-m-toluamide (DEET), limonene, linalool, citronellal, menthol, menthone, hinokitiol, geraniol, eucalyptol, indoxacarb, carane-3,4-diol, orange oil, citronella oil, lemon oil, lemongrass oil, cinnamon oil, peppermint oil, spearmint oil and hyssop oil; or synergists such as piperonyl butoxide (PBO), octachlorodipropyl ether (S-421), N-(2-ethylhexyl)bicyclo[2.2.1]hept-5-ene-2,3-dicarboximide, isobornyl thiocyanatoacetate (IBTA) and N-(2-ethylhexyl)-1-isopropyl-4-methylbicyclo[2.2.2]oct-5-ene-2,3-dicarboximide are suitable.

The present agent usually controls ectoparasites for animals efficiently by employing onto animals by regional application methods such as spot-on application and pour-on application.

The spot-on application is a well-known method for controlling ectoparasites by dropping a liquid agent onto a skin at the back of blade bone of animal body.

The pour-on application is also a well-known method for controlling ectoparasites by pouring a liquid agent along the back line of animal body and having the liquid agent spread on the surface of the animal body.

The dosage of the present agent is usually about 0.01 to 10 mL and the dosage of the present compound is usually about 0.1 to 300 mg per 1 kg of animal weight.

For the present invention, and as the pests that are effectively controlled, suitable ectoparasites of farm animals such as cows and sheep, as well as pets such as dogs and cats, include, for example, Diptera such as *Musca hervei, Musca bezzii, Haematobia irritans, Simulium iwatens, Culicoides oxystoma, Tabanus chrysurus, Culex pipiens* (common mosquito) and *Aedes albopictus*; Anoplura (lice) such as *Haematopinus eurysternus* and *Damalinia ovis*; Siphonaptera such as *Ctenocephalides felis* (cat flea), *Ctenophalides canis* (dog flea) and *Xenopsylla cheopis*; and Acarina (ticks) such as *Haemaphyxalis longicornis* and *Boophilus microplus*.

Furthermore, the objective animals that the present invention is employed upon, include the farm animals and pets mentioned above, and others, for example, Rodentia such as mice, rats, hamsters and squirrels; Lagomorpha such as rabbits; Carnivora such as ferrets; birds such as ducks, chickens, doves; and the like.

EXAMPLES

The present invention is explained with the examples in detail below.

Formulation Example 1

Five parts by weight of 1-(tetrahydrofuran-3-yl)methyl-3-methyl-2-nitroguanidine (hereinafter, Compound A), 50 parts by weight of hexamethylene glycol and 45 parts by weight of isopropanol are mixed to obtain a formulation.

Formulation Example 2

Five parts by weight of Compound A, 50 parts by weight of propylene glycol monomethyl ether and 45 parts by weight of dipropylene glycol are mixed to obtain a formulation.

Formulation Example 3

Five parts by weight of Compound A, 0.5 part by weight of pyriproxyfen, 50 parts by weight of propylene glycol monomethyl ether and 44.5 parts by weight of isopropanol are mixed to obtain a formulation.

Formulation Example 4

Five parts by weight of Compound A, 85 parts by weight of propylene glycol monomethyl ether and 10 parts by weight of d-limonen are mixed to obtain a formulation.

Formulation Example 5

Ten parts by weight of Compound A, 1 part by weight of pyriproxyfen, 30 parts by weight of diethylene glycol monoethyl ether and 59 parts by weight of benzyl alcohol are mixed to obtain a formulation.

Formulation Example 6

Ten parts by weight of Compound A, 50 parts by weight of diethylene glycol monoethyl ether and 40 parts by weight of benzyl alcohol are mixed to obtain a formulation.

The formulation obtained in Formulation example 6 can be applied by spreading onto the skin at the back of blade bone of a cat (about 3 kg in weight) for controlling fleas living on the cat. In this case, the dosage is usually about 0.4 mL.

Test Example 1

Formulations 1 through 7 were obtained by dissolving 5 parts by weight of Compound A into a previously prepared mixed solution of tripropylene glycol (hereinafter, TPG) and isopropanol (hereinafter, IPA) wherein the parts by weight of each preparation of 7 possibilities is 0:95, 10:85, 30:65, 50:45, 70:25, 80:15 and 95:0.

One fiftieths milliliters (0.02 mL) was dropped onto the neck area epidermis of a mouse (weight: about 30 g). Said mouse was hold and fastened with a metal net, and placed into a 900 mL glass canister. Twenty adult cat fleas were deposited into said canister so the mouse is infested. One day after infestation, the mortality was examined. Each was repeated thrice. The results are given in table 1.

TABLE 1

| Test # | Formulation | TPG/IPA (wt/wt) | Compound A/ TPG (wt/wt) | Mortality of Cat fleas (%) |
|---|---|---|---|---|
| 1-1(Comparative) | 1 | 0/95 | 5/0 | 38.3 |
| 1-2 | 2 | 10/85 | 5/10 | 55.0 |
| 1-3 | 3 | 30/65 | 5/30 | 75.0 |
| 1-4 | 4 | 50/45 | 5/50 | 80.0 |
| 1-5 | 5 | 70/25 | 5/70 | 93.3 |
| 1-6 | 6 | 80/15 | 5/80 | 75.0 |
| 1-7 | 7 | 95/0 | 5/95 | 60.0 |

Test Example 2

Ten parts by weight of Compound A was mixed with 90 parts by weight of diethylene glycol monoethyl ether and dissolved to afford a spot-on formulation.

Thirty cat flea adults were deposited on a cat (weight: 3.4 kg) and an elizabethan collar was put on the neck of the cat the day before application of the above formulation. Two fifths mililiters (0.4 mL) of the above spot-on formulation was spread onto the skin at the back of blade bone of the cat. Then, one day and three days after application, the number of infested fleas was counted by using a comb for gathering fleas. All the counted fleas were re-deposited on the cat after counting.

In addition, as a blank, cat fleas were deposited on a cat without application of the formulation by the same method as above, the number of the cat fleas was observed and controlling ratio was calculated by the following formula:

Controlling ratio (%)=(C−T)÷C×100

C: Infesting ratio of fleas in the case without application
T: Infesting ratio of fleas in the case with application of the formulation Each was repeated twice and the result are given in table 2.

TABLE 2

|  |  | One day after application | Three days after application |
|---|---|---|---|
| treated with spot-on formulation | Infesting ratio | 3.3 | 1.7 |
|  | Controlling ratio | 95.6 | 97.5 |
| blank (no treatment) | Infesting ratio | 75.0 | 66.7 |

What is claimed is:

1. An ectoparasite-controlling method for animals comprising:
    applying an ectoparasite-controlling agent to the body surface of an animal, wherein said ectoparasite-controlling agent comprises:
        0.1 to 20% by weight of 1-(tetrahydrofuran-3-yl)methyl-3-methyl-2-nitroguanidine, 10 to 95% by weight of a glycol or glycol monoalkyl ether and 3 to 70% by weight of a solvent selected from the group consisting of benzyl alcohol, propylene carbonate, and N-methyl-2-pyrrolidone.

2. The ectoparasite-controlling method according to claim 1, wherein the glycol or glycol monoalkyl ether is at least one selected from the group consisting of ethylene glycol, diethylene glycol, triethylene glycol, propylene glycol, dipropylene glycol, tripropylene glycol, hexamethylene glycol, 1,3-butanediol, 3-methyl-1,2-butanediol, 2-methyl-1,3-propanediol, ethylene glycol monomethyl ether, ethylene glycol monoethyl ether, ethylene glycol monobutyl ether, diethylene glycol monomethyl ether, diethylene glycol monoethyl ether, propylene glycol monomethyl ether, propylene glycol monoethyl ether, propylene glycol monotertiarybutyl ether, dipropylene glycol monomethyl ether and 3-methoxy-3-methyl-1-butanol.

3. The ectoparasite-controlling method according to claim 1, wherein the solvent is benzyl alcohol.

4. An ectoparasite controlling agent for animals which is a liquid formulation comprising 0.1 to 20% by weight of 1-(tetrahydrofuran-3-yl)methyl-3-methyl-2-nitroguanidine, 10 to 95% by weight of a glycol or glycol monoalkyl ether and 3 to 70% by weight of a solvent selected from the group consisting of benzyl alcohol, propylene carbonate, and N-methyl-2-pyrrolidone.

5. The ectoparasite-controlling agent according to claim 4, wherein the solvent is benzyl alcohol.

* * * * *